(12) United States Patent
McLaughlin

(10) Patent No.: US 9,326,720 B2
(45) Date of Patent: May 3, 2016

(54) WIRELESS, IMPLANTABLE ELECTRO-ENCEPHALOGRAPHY SYSTEM

(75) Inventor: Bryan McLaughlin, Cambridge, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 899 days.

(21) Appl. No.: 13/369,724

(22) Filed: Feb. 9, 2012

(65) Prior Publication Data
US 2012/0203079 A1 Aug. 9, 2012

Related U.S. Application Data

(60) Provisional application No. 61/441,115, filed on Feb. 9, 2011.

(51) Int. Cl.
| | |
|---|---|
| *A61B 5/04* | (2006.01) |
| *A61B 5/00* | (2006.01) |
| *A61B 5/0478* | (2006.01) |
| *A61N 1/05* | (2006.01) |
| *A61N 1/36* | (2006.01) |

(52) U.S. Cl.
CPC ........... *A61B 5/4094* (2013.01); *A61B 5/04012* (2013.01); *A61B 5/0478* (2013.01); *A61N 1/0531* (2013.01); *A61N 1/36064* (2013.01); *A61N 1/36139* (2013.01); *A61B 2560/0219* (2013.01)

(58) Field of Classification Search
CPC .......... A61B 5/4094; A61B 5/04001–5/04004; A61B 5/0476–5/04847; A61N 1/36082
USPC .................. 600/378, 544, 545, 546
See application file for complete search history.

(56) References Cited

U.S. PATENT DOCUMENTS

| | | |
|---|---|---|
| 7,676,263 B2 | 3/2010 | Harris et al. |
| 7,787,945 B2 | 8/2010 | Greene |

(Continued)

FOREIGN PATENT DOCUMENTS

| | | | |
|---|---|---|---|
| WO | WO 2007/058950 | * | 5/2007 |
| WO | WO-2007/058950 A2 | | 5/2007 |

OTHER PUBLICATIONS

International Search Report and Written Opinion in PCT/US2012/024485 dated Aug. 13, 2013.

(Continued)

*Primary Examiner* — Patricia Mallari
*Assistant Examiner* — Tiffany Weston
(74) *Attorney, Agent, or Firm* — Edward A. Gordon; Foley & Lardner LLP

(57) ABSTRACT

An electro-encephalography system includes an internal device for implantation below a scalp and above a skull of a patient, and an external device to be worn or carried outside the patient's body. The internal device includes a first electrode for receiving neurological signals originating from the patient's brain and a second electrode for receiving artifacts originating from sources other than the patient's brain. The external device includes a processing unit for receiving data from the internal device, mitigating the effects of the artifacts, and determining a neurological state of the patient. A therapy device is included to provide a therapy to the patient based on the patient's neurological state.

16 Claims, 14 Drawing Sheets

(56) References Cited

U.S. PATENT DOCUMENTS

| | | | |
|---|---|---|---|
| 7,930,035 B2 | 4/2011 | DiLorenzo | |
| 8,036,736 B2 | 10/2011 | Snyder et al. | |
| 2002/0103512 A1 | 8/2002 | Echauz et al. | |
| 2004/0138580 A1 | 7/2004 | Frei et al. | |
| 2005/0076908 A1 | 4/2005 | Lee et al. | |
| 2005/0090756 A1* | 4/2005 | Wolf et al. | 600/546 |
| 2006/0167371 A1* | 7/2006 | Flaherty et al. | 600/545 |
| 2006/0173510 A1 | 8/2006 | Besio et al. | |
| 2007/0167991 A1 | 7/2007 | DiLorenzo | |
| 2008/0091090 A1 | 4/2008 | Guillory et al. | |
| 2008/0234598 A1 | 9/2008 | Snyder et al. | |
| 2009/0228066 A1* | 9/2009 | Hirata et al. | 607/45 |
| 2011/0166430 A1 | 7/2011 | Harris et al. | |
| 2011/0213222 A1 | 9/2011 | Leyde et al. | |
| 2011/0224528 A1 | 9/2011 | Choi et al. | |
| 2011/0319785 A1 | 12/2011 | Snyder et al. | |

OTHER PUBLICATIONS

International Search Report in PCT/US2012/024485 dated May 10, 2012.

Stieglitz T et al: "Flexible BIOMEMS with electrode arrangements on front and back side as key component in neural prostheses and biohybrid systems", Sensors and Actuators B: Chemical: International Journal Devoted to Research and Development of Physical and Chemical Transducers, Elsevier S.A, Switzerland, vol. 83, No. 1-3, Mar. 15, 2002, pp. 8-14, XP004344478.

"Implanted EEG Device Predicts Epilepsy Seizures, Gives Opportunity for Patients to Make Themselves Safe," (Dec. 6, 2011) available at http://neurogadget.com/2011/12/06/implanted-eeg-device-predicts-epilepsy-seizures-gives-opportunity-for-patients-to-make-themselves-safe/3342.

Pedro Irazoqui-Pastor et al. "In-Vivo EEG Recording Using a Wireless Implantable Neural Transceiver," First International IEEE EMBS Conference on Neural Engineering, Mar. 20-22, 2003, pp. 622-625.

* cited by examiner

WIRELESS, IMPLANTABLE ELECTRO-ENCEPHALOGRAPHY SYSTEM

CROSS-REFERENCE TO RELATED APPLICATION

This application claims priority to and the benefit of, and incorporates herein by reference in its entirety, U.S. Provisional Patent Application No. 61/441,115, which was filed on Feb. 9, 2011.

TECHNICAL FIELD

In various embodiments, the invention relates to a wireless, implantable brain electro-encephalography ("EEG") system. In particular, embodiments of the invention relate to monitoring EEG signals wirelessly by using an implanted transducer and a wireless communications link.

BACKGROUND

Epilepsy is a disorder characterized by chronic, recurring seizures, resulting from uncontrolled discharges of electrical activity in the brain. A seizure typically manifests itself as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool.

There have been a number of proposals from groups around the world for predicting seizures and warning the patient of the impending seizure. Most of such proposals attempt to analyze the patient's electroencephalogram or electrocorticograms (referred to collectively as "EEGs"), to differentiate between a "pre-seizure condition" and a "between-seizures condition."

In the past, scalp EEG electrodes have been employed to record electrical activity produced along a human's scalp by the firing of neurons within the brain, as have headband arrays and cap electrodes. Unfortunately, these devices suffer from a number of disadvantages, including that they cannot typically be used in a convenient manner for chronic monitoring due to functional and aesthetic limitations. Scalp electrodes, for example, are generally unsuitable for measuring through the dead skin layer, which is approximately 30 microns thick, and typically require an electrolyte gel to increase the measurement repeatability.

In addition, current procedures generally result in electrodes having to be applied daily within the hospital and the patient's head being wrapped with tape. Typically, this can only be done for a maximum of seven consecutive days due to the instability of the electrode-tissue interface. For example, after multiple days, the skin may become brittle and irritated from the presence of the electrodes. In addition, patients may be cosmetically limited with bandaged electrodes around their head while the electrodes are on. Other electrodes have been designed for the scalp or for the cortex of the brain by numerous people, but they are typically battery powered and wired systems that require a craniotomy.

Current procedures also suffer from inaccuracies associated with artifact signals originating from locations other than the patient's brain. For example, muscle movements within the patient's scalp or eyes (e.g., blinking) create artifacts that are detected by the EEG electrodes, making it difficult to distinguish true neurological signals from other types of signals (i.e., noise). The artifacts may lead to erroneous determinations of the neurological state and/or erroneous predictions of neurological events, such as seizures.

Needs exist, therefore, for an improved EEG system and methods of use thereof. In particular, needs exist for EEG systems and methods that provide continuous monitoring of neurological signals and accurate predictions of neurological events.

SUMMARY OF THE INVENTION

In various embodiments, the present invention features an EEG micro-system that can be implanted under the scalp (but outside the cranium) of a human being and that can be used to record neurological signals, primarily from electrodes that are also positioned under the scalp. Alternatively, or additionally, the EEG micro-system may be used to transmit data (e.g., data related to the neurological signals) wirelessly to a nearby recorder. An external device may also be employed to measure inertial movement and/or cardiac pulse information. In particular embodiments, the EEG system is used in chronic epilepsy monitoring, in sleep applications (e.g., in sleep apnea applications), and/or in soldier 'dead-or-alive' applications. Moreover, the EEG system may provide closed-loop stimulation therapies, such as, for example, focused ultrasound, transcranial electrical stimulation, optical (e.g., light or photon) stimulation, radio-frequency stimulation, and/or transcranial magnetic stimulation.

The systems and methods described herein provide significant improvements in the ability to predict neurological events, such as seizures. For example, by implanting EEG sensors under the scalp and above the skull of the patient, the systems and methods provide a minimally invasive technique for prolonged patient monitoring, without the risks associated with a craniotomy (i.e., intra-cranial devices) and/or the comfort and cosmetic issues associated with external devices, such as scalp electrodes. Additionally, the use of separate electrodes or double-sided electrodes for direct measurement of artifacts allows the artifacts to be easily identified and eliminated from consideration. Removal of artifacts allows EEG signals to be monitored with minimal interference, thereby enabling the patient's neurological condition to be accurately assessed and neurological events to be reliably predicted.

In general, in one aspect, embodiments of the invention relate to an electro-encephalography system. The system includes (a) an internal device for implantation below a scalp and above a skull of a patient, and (b) an external device in wireless communication with the internal device. The internal device includes: (i) a first electrode for receiving a first signal having neurological signals originating from the patient's brain and artifacts originating from sources other than the patient's brain; (ii) a second electrode for receiving a second signal having the artifacts; and (iii) a therapy device for providing therapy to the patient. The first signal features a first ratio of the neurological signals to the artifacts. The external device is to be worn or carried outside the patient's body and includes a processing unit for: (i) providing power to the internal device; (ii) receiving data (including the first and second signals) from the first and second electrodes; (iii) processing the data received from the first and second electrodes to obtain a processed signal; (iv) determining a neurological state (e.g., a propensity for a seizure) of the patient based on the processed signal; and (v) transmitting instructions to the therapy device for providing therapy to the patient according to the neurological state. The processed signal features a second ratio of the neurological signals to the artifacts, which is greater than the first ratio. The external device may include an earpiece.

In general, in another aspect, embodiments of the invention relate to a method of performing electro-encephalography. The method includes receiving, at a first electrode implanted below a scalp and above a skull of a patient, a first signal that includes neurological signals originating from a patient's brain and artifacts originating from sources other than the patient's brain. The first signal features a first ratio of the neurological signals to the artifacts. The method also includes receiving, at a second electrode implanted below the scalp and above the skull of the patient, a second signal including the artifacts; receiving data (including the first and second signals) from the first and second electrodes at a processing unit; processing the data received from the first and second electrodes to obtain a processed signal; determining a neurological state (e.g., a propensity for a seizure) of the patient based on the processed signal; and transmitting instructions to a therapy device for providing therapy to the patient according to the neurological state. The therapy device is also implanted below the scalp and above the skull of the patient. The processed signal features a second ratio of the neurological signals to the artifacts, which is greater than the first ratio. In certain embodiments, determining the neurological state of the patient includes monitoring the data received from the first and second electrodes to provide a patient-specific indicator of seizure onset and/or a patient-specific indicator of an artifact. Processing the data may include, for example, subtracting or removing the second signal from the first signal.

In certain embodiments, at least one of the processed signal or the data received from the first and second electrodes is recorded (e.g., using the processing unit). The therapy device may include, for example, one or both of the first and second electrodes. Moreover, the first and second electrodes may be disposed within a double-sided electrode. In various embodiments, the therapy provided to the patient includes electrical stimulation, acoustic stimulation, RF stimulation, ultrasound stimulation, magnetic stimulation, electro-magnetic stimulation, photon (e.g., optical) stimulation, and/or a pharmaceutical compound. In one embodiment, the second electrode is configured for implantation in a muscle artifact location. The artifacts may originate from, for example, the patient's scalp, the patient's eyes, electromyographic signals, and motion.

In various embodiments, trans-cutaneous wireless power is provided (e.g., by the processing unit) to the internal device (e.g., to the first and second electrodes). The external device may include a sensor for sensing the patient's temperature, cardiac pulse-rate, and/or tissue oxygenation level. In one embodiment, the external device includes an inertial sensor for sensing a heading, a motion, or an orientation of the processing unit. The external device may include an audible alarm for warning the patient of an onset of a seizure. Data may be transmitted from the external device to a remote computer using, for example, a modem or a transceiver. In certain embodiments, the neurological state of the patient is determined based on data received from the first and second electrodes in response to stimulation of the patient's brain.

These and other objects, along with advantages and features of embodiments of the present invention herein disclosed, will become more apparent through reference to the following description, the figures, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DESCRIPTION

In certain embodiments, the present invention relates generally to systems and methods for monitoring a patient's neurological condition. Various embodiments of the invention feature an EEG system that includes one or more electrodes configured to be implanted under the scalp (but outside the skull) of the patient (e.g., a human being) and a signal processing system in communication with the electrode(s). The system can be employed to determine a neurological state of the patient and to provide a therapy to the patient according to the neurological state. For example, in certain embodiments, the system is used to predict onset of a seizure and to provide a therapy to the patient to prevent the seizure or to mitigate the effects of the seizure.

Figure 1:
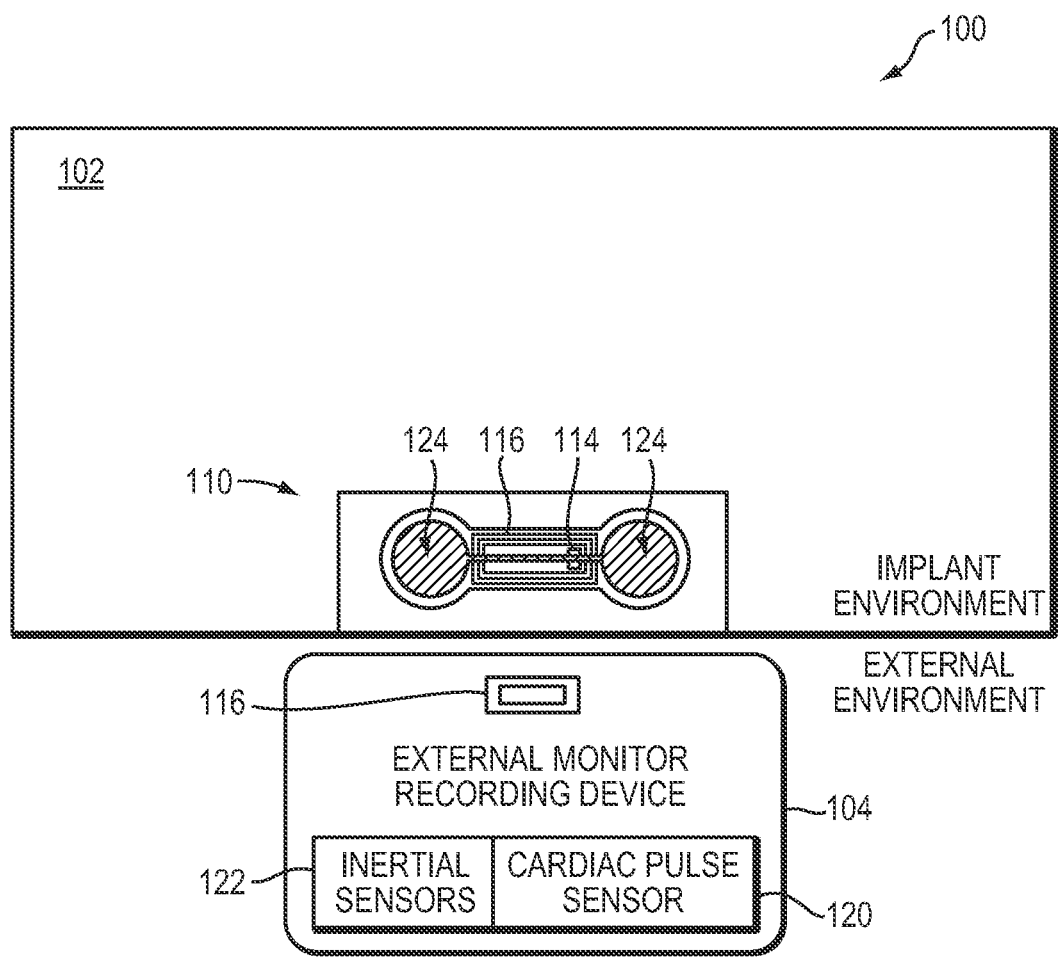
FIG. 1 is a schematic diagram of a system for determining a neurological state of a patient, in accordance with one embodiment of the invention.
Figure 2:
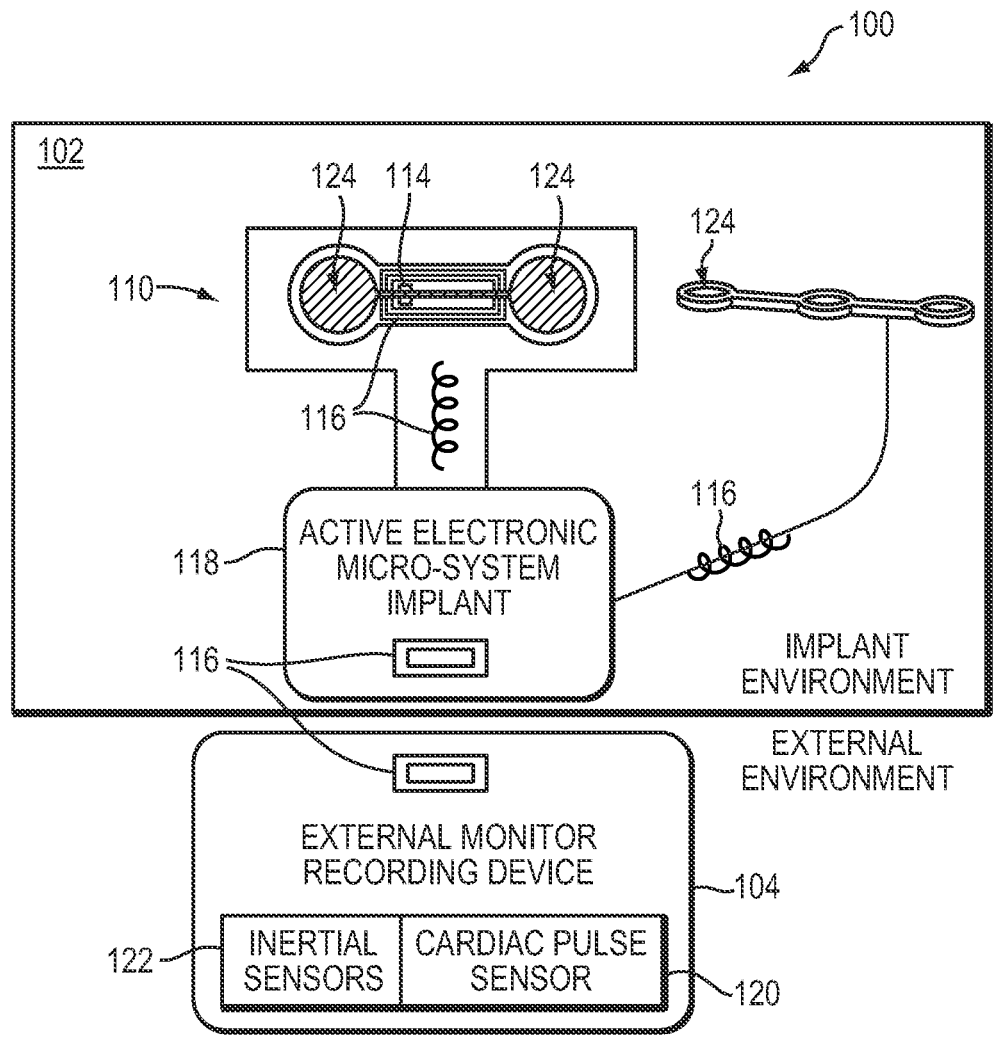
FIG. 2 is a schematic diagram of a system for determining a neurological state of a patient, in accordance with another embodiment of the invention.
Figure 3:
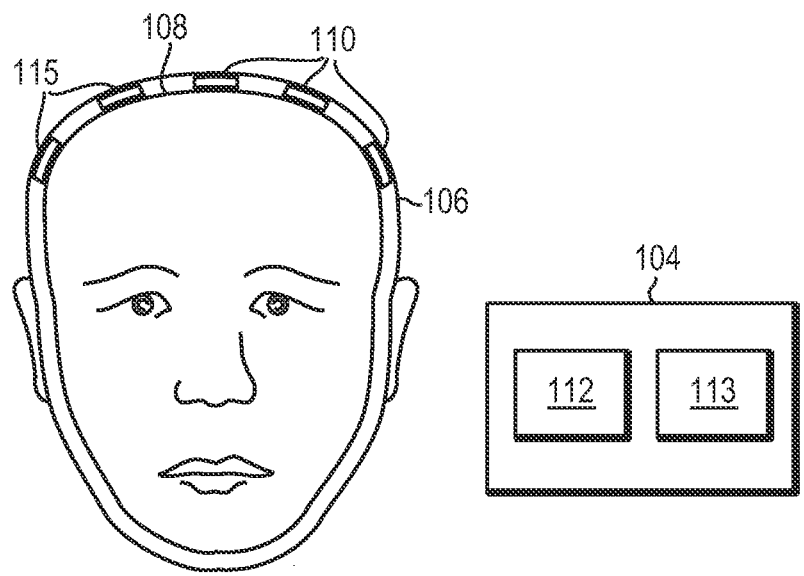
FIG. 3 is a front schematic view of a plurality of sensors implanted in a sub-galeal region of a patient for determining a neurological state of the patient, in accordance with one embodiment of the invention.

Referring to FIGS. 1 through 3, in certain embodiments, a system 100 for performing EEG includes an internal device 102 configured for implantation in a patient, and an external device 104 configured to be worn or carried outside of the patient's body (e.g., as an earpiece and/or a handheld device). In a preferred embodiment, the internal device 102 is implanted beneath a scalp 106 and above a skull 108 of the patient (i.e., in a sub-galeal region of the patient). The internal device 102 includes one or more sensors 110 for receiving neurological signals from a patient's brain. Data corresponding to the neurological signals may be wirelessly transmitted from the internal device 102 to the external device 104. The internal device 102 may also include components for stimulating the patient's brain or providing a therapy to the patient's brain. For example, the sensors may be configured to provide stimulation or some other therapy to the patient.

In certain embodiments, the external device 104 includes a microprocessor or processing unit 112 for analyzing the data received from the internal device 102, and computer memory 113 for storing the received and/or processed data. For example, the processing unit 112 may determine a neurological state of the patient and/or predict a neurological event (e.g., a seizure). Depending on the neurological state, the processing unit 112 may also instruct a therapy device 115 in the internal device 102 to deliver a therapy (e.g., electrical stimulation, RF stimulation, acoustic stimulation, ultrasonic stimulation, magnetic stimulation, and/or light stimulation) to the patient.

In various embodiments, the system 100 includes active electronics 114 and/or coils 116 (e.g., inductive coils) for wireless communication and/or power transmission between the internal device 102 and the external device 104. For example, coils 116 may be used in transmitting wireless power from the external device 104, which includes or is connected to a power source (e.g., a battery), to the internal device 102, which need not include a separate power source. The active electronics 114 and/or the coils 116 may be disposed on a sensor 110. Referring to FIG. 2, the internal device 102 may include a micro-system 118 having the active electronics 114 and/or the coils 116. In one embodiment, the micro-system 118 is connected to one or more sensors 110 using a wire, although a wireless connection may also be utilized.

In certain embodiments, the external device 104 and/or the internal device 102 include optical and/or electrical sensing components, which allow cardiac pulse-rate and tissue oxygenation to be measured and/or inferred. For example, a cardiac pulse sensor 120 may be included in the external device 104 and/or internal device 102. The external device 104 and/or internal device 102 may also contain inertial sensors 122, which, for example, determine the heading, motion, and/or orientation of the patient. In one embodiment, the external device 104 infers a condition of the patient (e.g., neurological state) using data obtained from the internal sensor(s) 110, the cardiac pulse sensor 120, the tissue oxygenation sensor, and/or the inertial sensors 122. The external device 104 may record, process, and store information (e.g., neurological data) received from the internal device 102.

Figure 4:
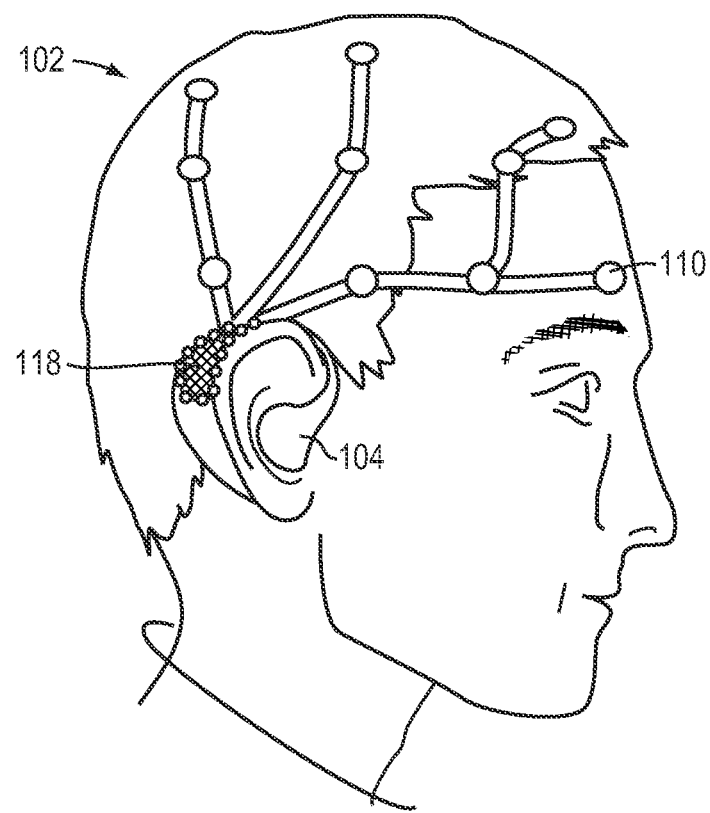
FIG. 4 is a schematic perspective view of a patient outfitted with a system for determining a neurological state of the patient, in accordance with one embodiment of the invention.

In various embodiments, the system (e.g., the internal device 102 and/or the external device 104) includes an energy storage device (e.g., a capacitor or a battery), a temperature monitor, a microprocessor and memory, a pulse or frequency generator for stimulation therapy, a multi-channel amplifier, a stimulation transducer (e.g., radio-frequency, electrical, optical, and/or acoustic), an antenna, a coil (e.g., an inductive coil), and/or a wireless transmitter. In one embodiment, the sensor includes one or more recording, reference, or driving electrodes 124. In various embodiments, the implanted micro-system 118 operates primarily from external power, applied using wireless power transmission across the scalp. Referring to FIG. 4, in certain embodiments, at least a portion of the external device 104 (e.g., an earpiece) is disposed over (e.g., adjacent to or on top of) the implanted internal device 102, and provides trans-cutaneous wireless power from outside the scalp or skin. The sensors 110 may extend from the implanted micro-system 118, below the scalp.

In certain embodiments, the external device 104 serves as a signal processor that identifies significant neural events. For example, the processing unit 112 of the external device 104 may analyze data received from the sensor 110 to detect a seizure, or monitor wakefulness or sleepiness. The external device 104 may also feature an audible alarm (for example to warn of the onset of a seizure), as well as a modem or wireless component that may connect to a handheld device (e.g., a cellular phone), a home computer, or to a health monitoring network. The handheld device may itself contain other signal processing electronics, displays, alarms, etc.

Figure 5:
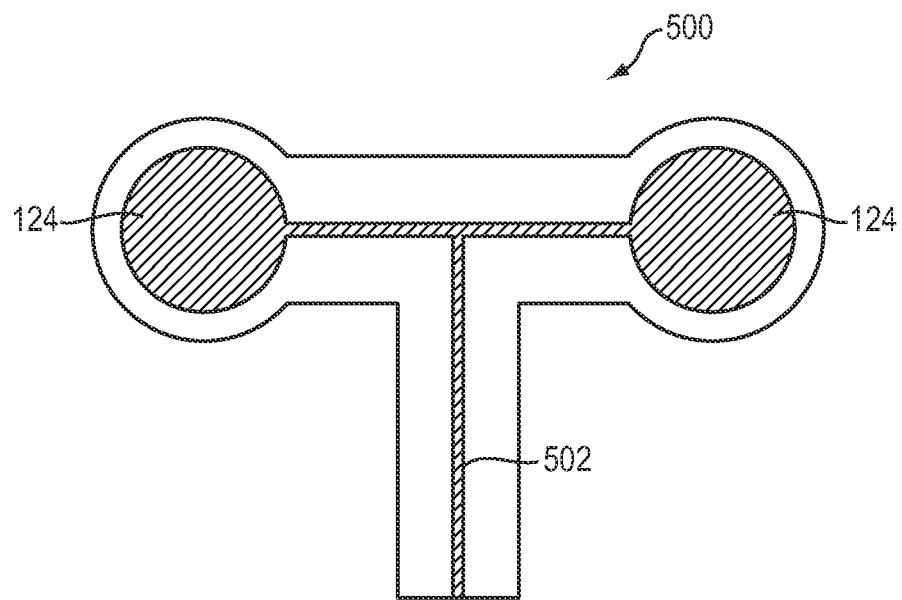
FIG. 5 is a top schematic view of a sensor having two electrodes for detecting neurological signals, in accordance with one embodiment of the invention.

In various embodiments, the sensors 110 of the internal device 102 include electrodes 124, in the form of metallic wires or disks, and active and/or passive circuitry. FIG. 5 depicts a passive sensor 500 having two disk-shaped electrodes 124 and a wire 502 or wired interface for connecting the sensor 500 to other system components (e.g., the micro-system 118).

Figure 6:
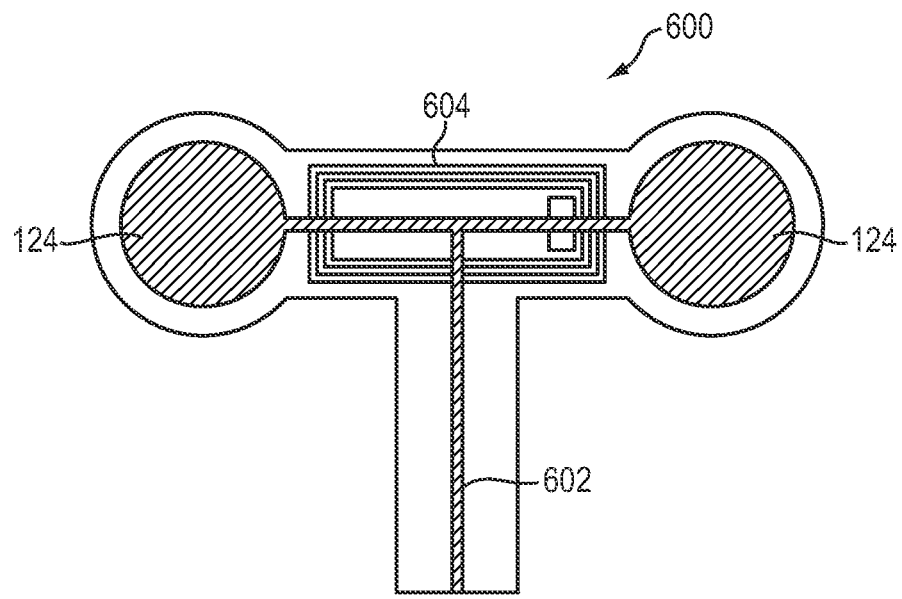
FIG. 6 is a top schematic view of a sensor having two electrodes and active circuitry for detecting neurological signals, in accordance with one embodiment of the invention.

FIG. 6 depicts an active sensor 600 having two disk-shaped electrodes 124, a wire 602, and active circuitry 604. The active circuitry 604 may be used, for example, to wirelessly communicate with other portions of the internal device 102 (e.g., other sensors, the micro-system 118, and/or a therapy device) and/or the external device 104. In one embodiment, the active circuitry 604 is used to process signals received by the electrodes 124, provide signal conditioning, and/or provide instructions for delivering therapy to the patient.

Figure 7:
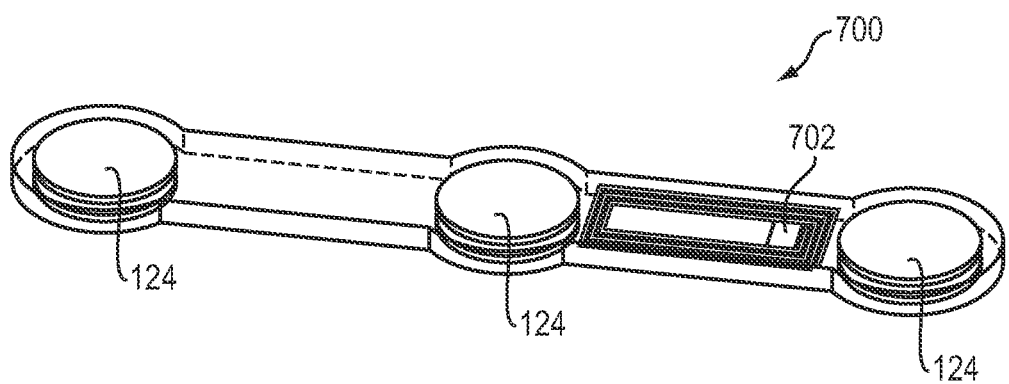
FIG. 7 is a perspective schematic view of a sensor having three electrodes and active circuitry for detecting neurological signals, in accordance with one embodiment of the invention.

Referring to FIG. 7, a sensor 700 may include more than two electrodes 124 (e.g., three, as shown) with active and/or passive circuitry 702. The electrodes 124 may be arranged in any pattern or configuration within the sensor 700, for example in a line or in a grid. As mentioned, the sensor 700 may include a coil to enable wireless power and/or wireless data transfer.

In various embodiments, the active circuitry located on the sensors and/or within the implanted micro-system amplify and digitize recorded signals. The active circuitry may include, for example, a filmed microcircuit or a printed circuit board ("PCB") having active components (e.g., integrated circuits, ASICs, memory, etc.) and passive components (e.g., resistors, capacitors, etc.). The sensors may include a rechargeable or non-rechargeable power supply (e.g., batteries), and/or x-ray visible markers. The system 100 may include any number of sensors, with each sensor having any number of electrodes, depending on the clinical indication and/or requirement.

Figure 8:
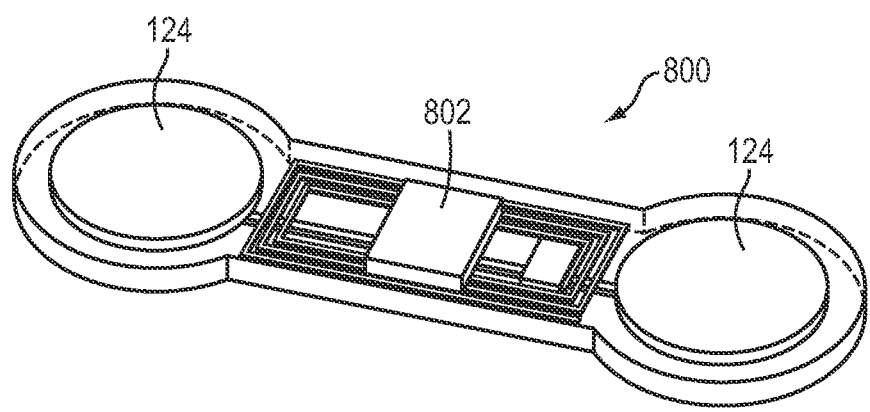
FIG. 8 is a perspective schematic view of a two-channel sensor having two electrodes and active circuitry for detecting neurological signals, in accordance with one embodiment of the invention.
Figure 9:
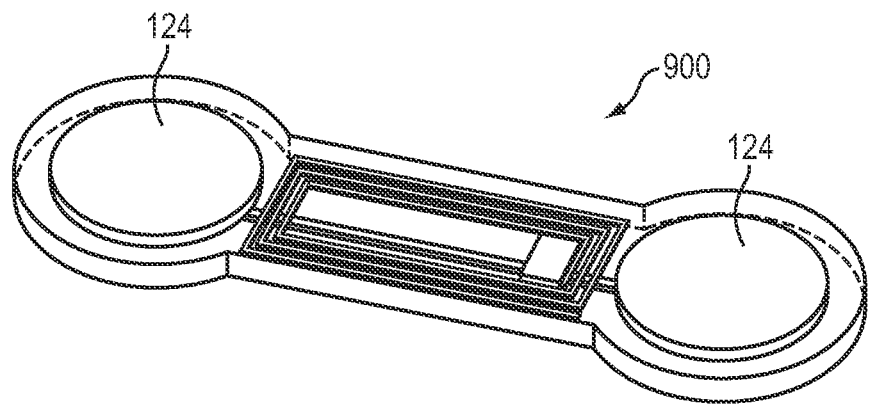
FIG. 9 is a perspective schematic view of a single-channel sensor having two electrodes and active circuitry for detecting neurological signals, in accordance with one embodiment of the invention.

Referring to FIG. 8, in certain embodiments, a sensor 800 includes a bipolar electrode with two circular pad transducers or electrodes 124 that are electrically referenced to a square central contact 802. The sensor 800 includes two channels. Referring to FIG. 9, in one embodiment, a sensor 900 includes two electrodes 124 that are referenced to one another in a differential pair application. The sensor 900 includes a single channel.

Figure 10:
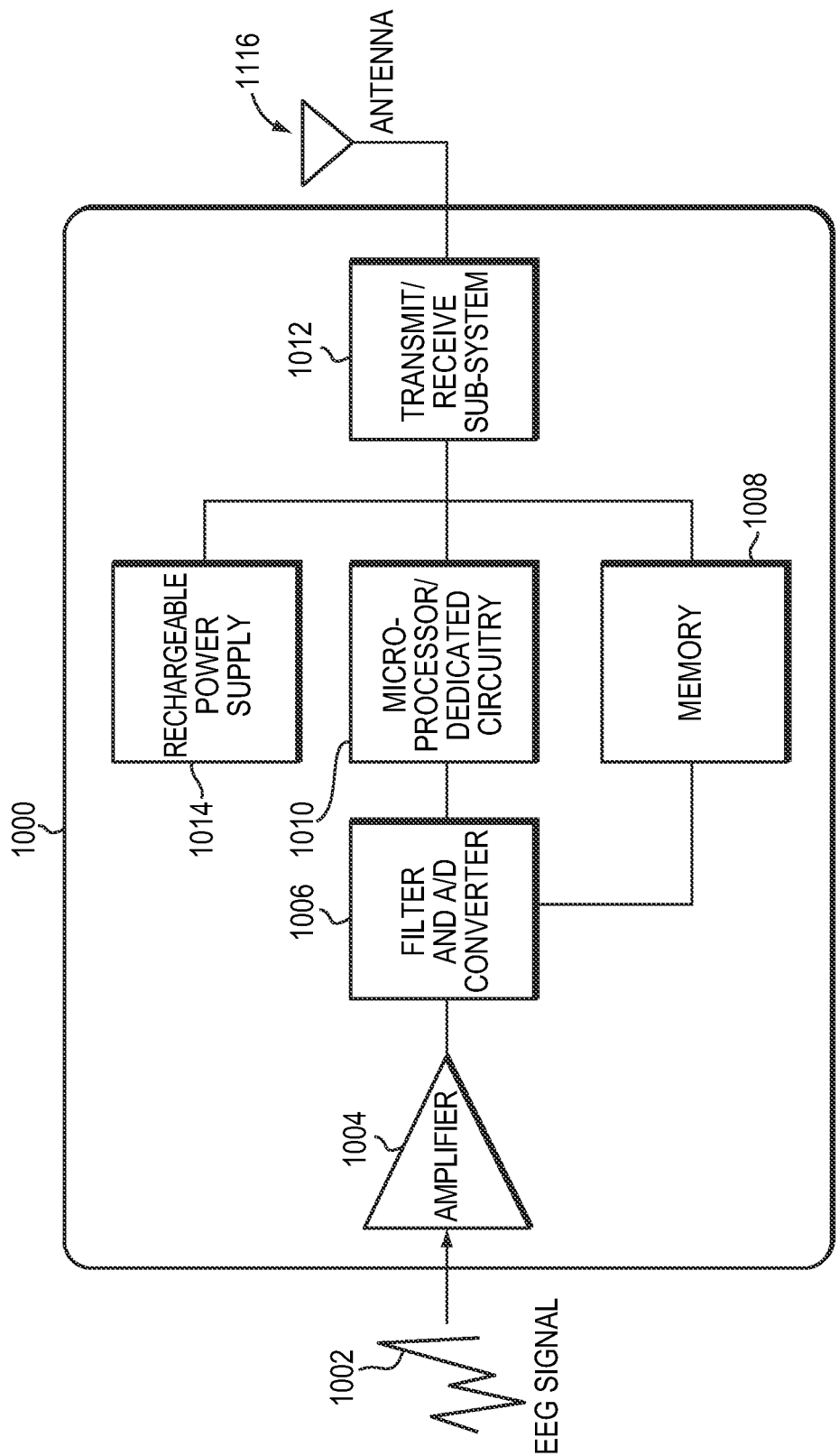
FIG. 10 is a schematic diagram of an internal device for detecting neurological signals, in accordance with one embodiment of the invention.

Referring to FIG. 10, in certain embodiments, a sensor 1000 of the internal device 102 is used to sample a physiological signal 1002 from the patient (e.g., an EEG signal), and to transmit the sampled signal to the external device 104. While it may be possible to record and transmit an analog EEG signal to the external device 104, the analog EEG signal will typically undergo processing before transmission to the external device 104. For example, the sensor 1000 may include a printed circuit board having an amplifier 1004, one or more filters 1006 (e.g., bandpass, notch, lowpass, and/or highpass), and an analog-to-digital converter 1006. In some embodiments, the sensor 1000 includes a memory 1008 (e.g., RAM, EEPROM, Flash, etc.) for permanently or temporarily storing or buffering the processed EEG signal 1002. The memory 1008 may be used, for example, as a buffer to temporarily store a processed EEG signal if there are problems with transmitting the data to the external device 104. For example, if the external device's power supply is low, if the memory 113 in the external device 104 is removed, or if the external device 104 is out of communication range with the internal device 102, the EEG signals may be temporarily buffered in memory 1008, and the buffered EEG signals and the current sampled EEG signals may be transmitted to the external device 104 when the problem has been corrected.

The sensor 1000 may optionally include dedicated circuitry and/or a microprocessor 1010 for further processing of the EEG signal 1002 prior to transmission to the external device 104. For example, the microprocessor 1010 may execute EEG analysis software, such as a seizure prediction algorithm, a seizure detection algorithm, safety algorithm, or portions of such algorithms. The microprocessor 1010 may send the analysis results to a transmit/receive sub-system 1012 for wireless transmission to the external device 104 and/or store the results in the memory 1008. In some embodiments, the sensor 1000 includes a rechargeable or non-rechargeable power supply 1014, such as a battery, a capacitor, or the like. In other embodiments, the sensor 1000 does not include its own power supply 1014, but is instead wirelessly powered by the external device 104, as described above. The sensor 1000 may also include an antenna 1016 for communicating with other sensors, the micro-system 118, and/or the external device 104.

In various embodiments, the internal device 102 includes one or more biocompatible materials, such as glass, titanium, ceramic, liquid crystal polymer, silicone, polyurethane, or other materials, that are inert and biocompatible to the human body and that are able to hermetically seal electronic components. The internal device 102 may also include a rigid material such as polycarbonate. Moreover, the internal device 102 may include one or more x-ray visible markers that allow for x-ray localization of the internal device 102 (e.g., the sensors).

In certain embodiments, the sensors of the internal device 102 are minimally invasive and are implanted with an introducer, trocar, or syringe-like device under local anesthesia by a physician or potentially even a physician's assistant. In one embodiment, the sensors have a longitudinal dimension from about 1 cm to about 10 cm, or less than about 3 cm. A lateral dimension of the sensors may be, for example, from about 0.5 mm to about 10 mm, or less than about 2 mm. As can be appreciated, such dimensions are merely illustrative, and other embodiments of implanted device may have larger or smaller dimensions.

Figure 11A:
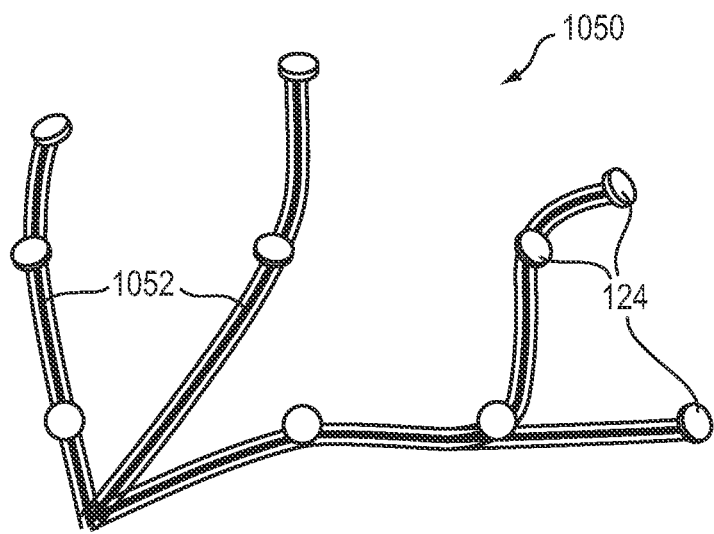
FIGS. 11a through 11c are schematic diagrams of sensors having multiple electrodes for detecting neurological signals, in accordance with one embodiment of the invention.
Figure 11B:
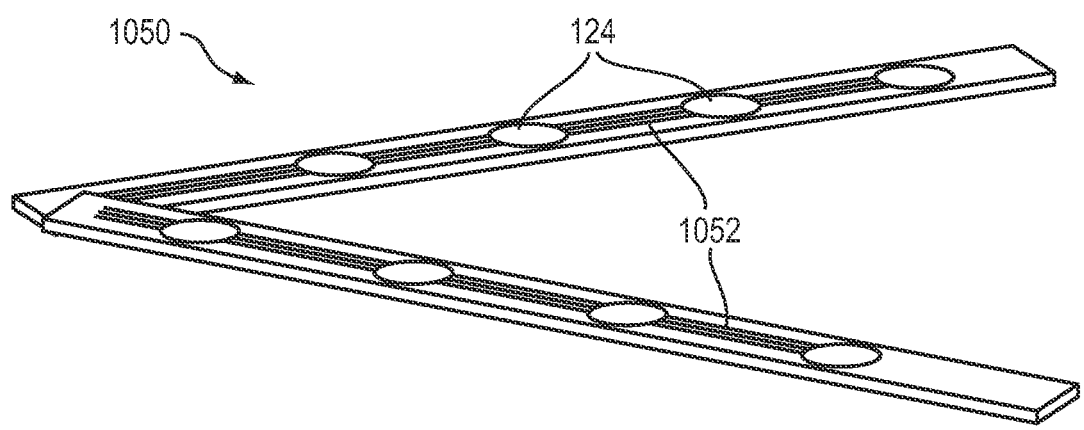
Figure 11C:
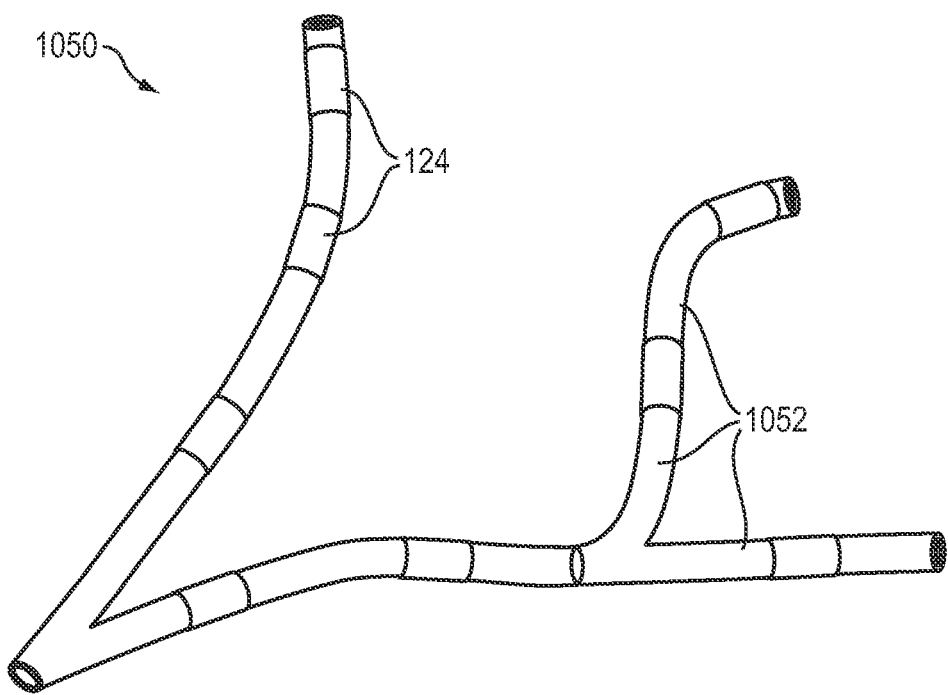

Referring to FIGS. 11a, 11b, and 11c, multiple sensors may be interconnected to form a sense or transduction array 1050 of electrodes 124. The electrodes 124 may be disposed on or within thin strips 1052 of material that are implanted under the patient's scalp. The strips 1052 and electrodes 124 may be flat, as shown in FIGS. 11a and 11b, or cylindrical or tubular, as shown in FIG. 11c.

In certain embodiments, the electrodes 124 of the sensors include or consist essentially of platinum, platinum-iridium alloy, stainless steel, or any other conventional electrode material, including metals and other conductive materials. The electrodes 124 may include a coating or surface treatment such as platinum-iridium, platinum-black, and/or TEFLON® to, for example, reduce electrical impedance. The electrodes 124 typically have a smooth or rounded shape to reduce tissue erosion. In one embodiment, a surface of each electrode is about 15 mm$^2$, or from about 1 mm$^2$ to about 50 mm$^2$. Smaller electrodes have the advantage of reducing the overall sensor size, which can be beneficial for improving patient comfort and reducing the risk of tissue erosion. Since electrode impedance is inversely proportional to electrode contact area, the impedance of small cylindrical electrode contacts is generally higher than larger disk electrodes. In one embodiment, disk electrodes result in more stable long-term recordings.

The sensor may have any desired shape and the electrodes 124 may be positioned at any position/orientation on the sensor. For example, the sensor may taper in one direction, be substantially spherical, substantially oval, substantially flat, or the like. Additionally or alternatively, the sensor may have one or more substantially planar surfaces so as to enhance the conformity to the patient's skull and to prevent rotation of the internal device 102. The sensor may optionally include a conductive electromagnetic interference shield (EMI) that is configured to shield electronic components on the sensor.

In certain embodiments, a spacing between the various electrodes 124 in a sensor is from about 2 mm to about 25 mm, or from about 5 mm to about 10 mm. In one embodiment, the electrode spacing is about 20 mm. Transducers used for stimulation may have a shorter spacing, such as, for example, from about 5 mm to about 15 mm. A thickness of the sensor may be about 2 mm, or from about 1 mm to about 5 mm.

In various embodiments, the implantable sensors are configured to continuously sample the brain activity of the groups of neurons in the immediate vicinity of the implanted device. Typically, the implantable sensor will be interrogated and/or powered by a signal from the external device 104 to facilitate the continuous sampling of the brain activity signals. Sampling of the brain activity (e.g., when recorded from outside the skull) is typically carried out at a rate below about 100 Hz, and preferably between about 1 Hz and about 60 Hz, but it could be higher or lower, depending on the specific condition being monitored, the patient, and other factors. Each sample of the patient's brain activity will typically contain between about 8 bits and about 32 bits, and preferably about 16 bits. Thus, if each return communication transmission to the external device 104 includes one EEG sample per transmission, and the sample rate is 100 Hz and there are 16 bits/sample, the data transfer rate from the implantable sensors to the external device 104 is at least about 1.6 Kbits/second. If there are 32 sensors, the total data transfer rate for the system would be about 51.2 Kbits/second. In alternative embodiments, it may be desirable to have the internal device 102 and sensors sample the brain activity of the patient in a non-continuous fashion. In such embodiments, the implantable sensors may be configured to sample the brain activity signals periodically (e.g., once every 10 seconds) or aperiodically.

Figure 12A:
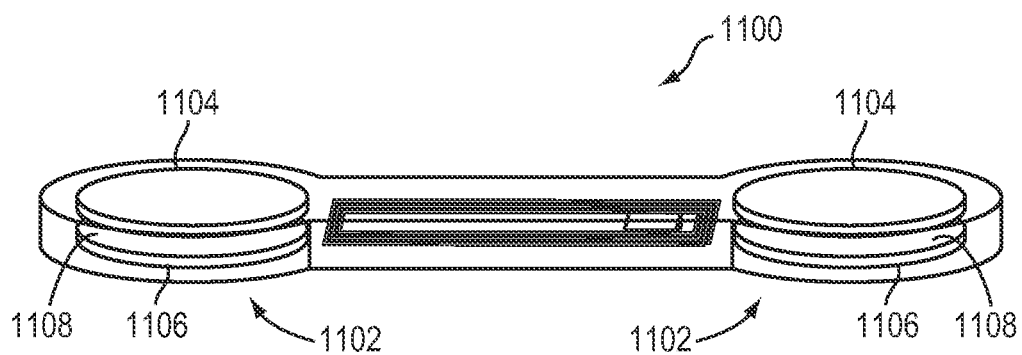
FIG. 12a is a perspective schematic view of a double-sided sensor for independently detecting neurological signals and artifacts, in accordance with one embodiment of the invention.
Figure 12B:
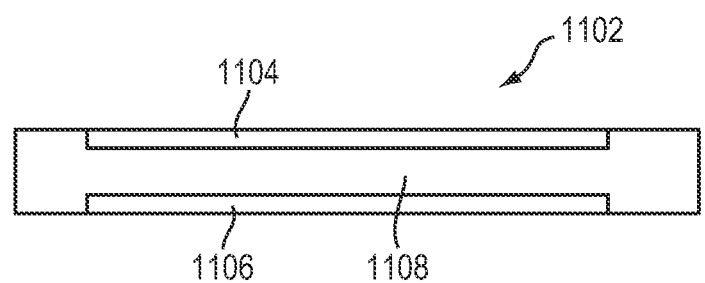
FIG. 12b is a side view of a double-sided electrode for independently detecting neurological signals and artifacts, in accordance with one embodiment of the invention.

Referring to FIGS. 12a and 12b, in various embodiments, a sensor 1100 of the internal device 102 includes a double-sided electrode 1102 having a top electrode 1104, a bottom electrode 1106, and a dielectric material 1108 between the top and bottom electrodes. The dielectric material 1108 may be, for example, a polymer, a biological material, or any other electrically insulating material. The sensor 1100 may be used to independently detect signals transmitted from opposite sides of the sensor 1100. For example, when the sensor 1100 is positioned in the sub-galeal region of a patient's head, the top electrode 1104 may be used to detect artifact signals arising from muscle movement in the patient's scalp and/or eyes, and the bottom electrode 1106 may be used to detect neurological signals originating from the patient's brain. The neurological signals will typically also be corrupted with artifacts. By independently detecting the two signals, the influence of the artifact signals may be mitigated or eliminated. For example, the signals from the top electrode 1104 may be used to distinguish and/or remove any artifacts (e.g., scalp muscle artifacts, myogenic potentials, motion artifacts, electromyography artifacts, ocular artifacts, etc.) present in the signals from the bottom electrode 1106. Scalp muscle artifacts have historically presented a significant problem in EEG measurement accuracy and associated determinations of a patient's neurological state.

In certain embodiments, artifacts are mitigated or eliminated using two or more electrodes (e.g., multiple single electrodes) implanted in different locations of a person's head. For example, a first electrode may be implanted at a first location to receive a first signal that includes neurological signals originating from the patient's brain. As mentioned, this first signal will typically also be corrupted with artifacts. At the same time, a second electrode may be implanted in a myogenic potential or muscle artifact region (e.g., near the eyes, forehead, and/or the temporalis muscles) to receive a second signal that primarily includes artifacts. By comparing the first and second signals, the artifacts may be distinguished from the neurological signals. In this way, any artifacts present in the first signal may be removed (at least partially) from the first signal to obtain a processed signal having the desired neurological information, with few or no artifacts.

Figure 13A:
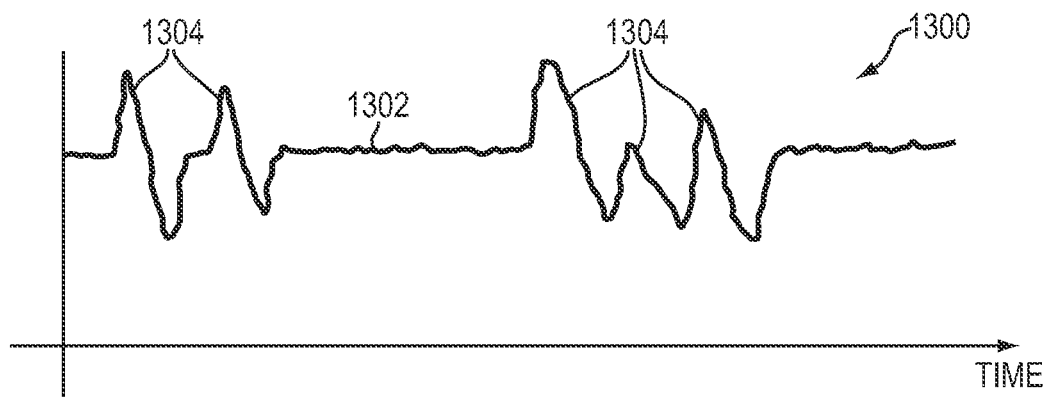
FIGS. 13a, 13b, and 13c depict plots of a first signal having a neurological signal and artifacts, a second signal having artifacts, and a processed signal having the neurological signal and no artifacts, respectively, in accordance with one embodiment of the invention.
Figure 13B:
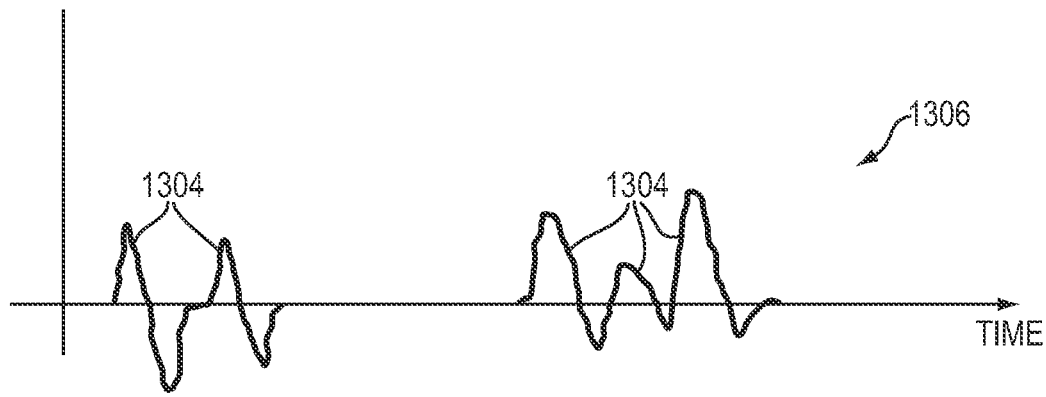
Figure 13C:
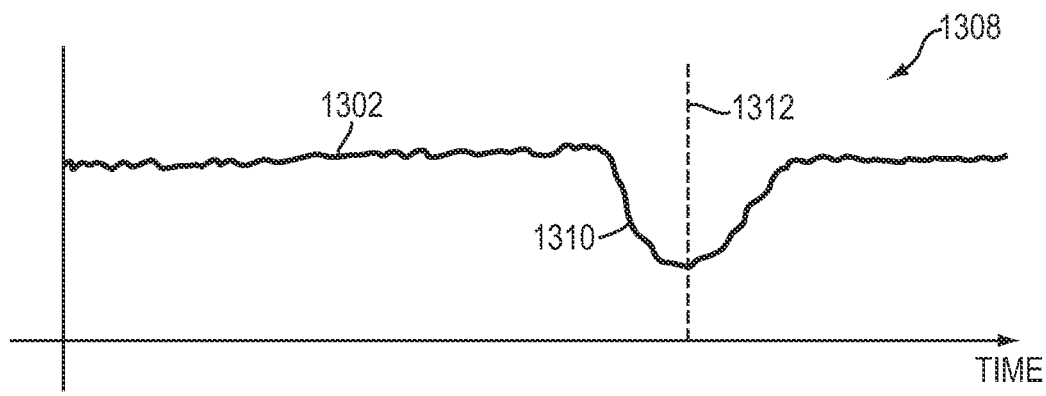

FIGS. 13a through 13c illustrate the removal of artifacts from a sensor signal, in accordance with certain embodiments of the invention. FIG. 13a depicts a first signal 1300 that includes a neurological signal 1302 from a patient's brain and artifacts 1304 from sources other than the patient's brain. FIG. 13b depicts a second signal 1306 that includes the artifacts 1304 from sources other than the patient's brain. The first and second signals 1300, 1306 may be obtained using the double-sided electrode 1102 and/or separate electrodes or sensors, as explained above. For example, the second signal 1306 may be obtained from a second sensor implanted in a muscle artifact location, away from the location of a first sensor used to obtain the first signal 1300.

Referring to FIG. 13c, the first and second signals 1300, 1306 may be processed to obtain a processed signal 1308 that facilitates the determination of the patient's neurological state. As depicted, the processed signal 1308 includes the neurological signal 1302 with no artifacts 1304, or with the artifacts 1304 at least partially removed. By removing the artifacts 1304, the processed signal 1308 reveals a temporary dip or drop 1310 in the neurological signal 1302 that is indicative of a neurological event 1312, such as a seizure. Advantageously, the processed signal 1308 makes it easier to detect the onset of the neurological event 1312, which may not be detectable in the first signal 1300.

In certain embodiments, the processed signal 1308 is obtained through signal processing techniques, including normalization, subtraction, frequency binning, and/or filtration. For example, the second signal 1306 may be amplified to make an amplitude of the artifacts 1304 in the second signal 1306 equal to an amplitude of the artifacts 1304 in the first signal 1300. The second signal 1306 may then be subtracted from the first signal 1300 to obtain the processed signal 1308. Prior to subtracting the signals, one or both of the first and second signals 1300, 1306 may be biased. For example, the second signal 1306 may be biased so that the signal is zero, on average, before the second signal 1306 is subtracted from the first signal 1300. By biasing the second signal 1306 in this manner, the processed signal 1308 may have an average value that is equal to an average value for the first signal 1300. In one embodiment, a frequency content of the artifacts 1304 is determined through frequency analysis of the second signal 1306, and the artifact frequency content is removed from the first signal 1300 to produce the processed signal 1308, using filtration techniques.

In various embodiments, active stimulation is employed to induce artifacts in spatial regions while recording of the artifacts is performed. These artifacts may subsequently be signal-processed by electronics in the internal device 102 (e.g., by the micro-system 118) and/or the external device 104 to enhance the detection and prediction of neural events. Identification and utilization of artifact signals enhances the determination of genuine neurological events (e.g., seizures).

In certain embodiments, and as previously mentioned, the systems described herein include one or more implantable sensors that are configured to sample electrical activity from the patient's brain (e.g., EEG signals). The implantable sensors may be implanted anywhere in the patient, but typically one or more of the sensors are implanted adjacent a previously identified epileptic focus or a portion of the brain where the focus is believed to be located. It may also be desirable to position one or more of the implantable sensors distal to the epileptic focus. The systems may be used to monitor a neurological condition of the patient for purposes of estimating the patient's susceptibility for a neurological event. Alternatively, or additionally, the systems may be used to help determine the location of the epileptic focus.

Figure 14:
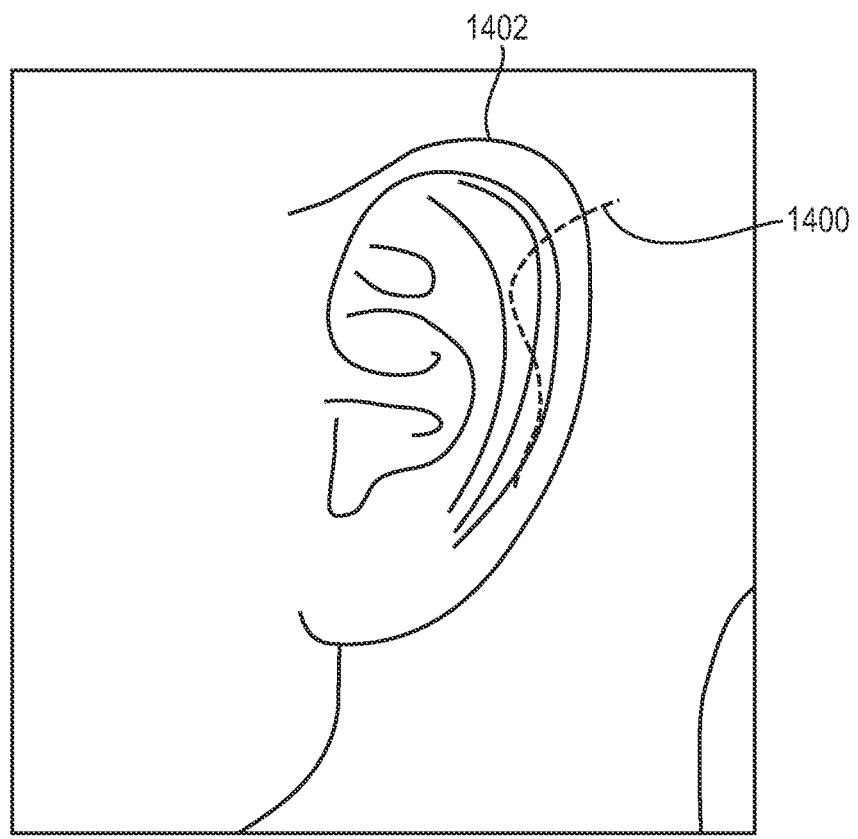
FIG. 14 is schematic side view of a patient's head indicating a location for implanting elements of a system for detecting neurological signals and artifacts, in accordance with one embodiment of the invention.

Referring to FIG. 14, in one embodiment, a method for implanting the internal device 102 includes making a small scalp flap 1400 behind a patient's ear 1402. The flap 1400 is wide enough to insert one or more sensors and/or the internal micro-system 118. The procedure for implanting the internal device 102 below the skin may be similar to those employed for implanting cochlear implants, as well understood by those of ordinary skill in the art, but may require a much smaller incision. The sensors are positioned beneath the scalp, for example in the sub-galeal space.

In certain embodiments, due to the small size of the internal device 102 (e.g., the sensors), the sensors and/or micro-system may be injected into the patient under local anesthesia in an out-patient procedure by the physician or neurologist.

Because the internal device 102 is implanted entirely beneath the skin, infection risk is reduced and there are minimal cosmetic implications.

If desired, the internal device 102 and/or the sensors thereof may include an anchoring assembly that improves the anchoring of the internal device 102 to the skull or the layers within the scalp. Such anchoring may be carried out with adhesive, spikes, barbs, protuberances, suture holes, sutures, screws, or the like.

Advantageously, in certain embodiments, the internal device 102 is able to monitor EEG signals from the patient without the use of burr holes in the skull or a craniotomy (e.g., implantation within the brain). This significantly reduces the risk of infection for the patient and makes the implantation process easier. While there may be some attenuation of the EEG signals and movement artifacts in the signals, because the internal device is below the skin, there may be much lower impedance than with scalp electrodes. Furthermore, the use of additional electrodes for measuring and removing artifacts, as described above, significantly improves the reliability and accuracy associated with seizure detection and prediction.

Alternative embodiments of the internal device 102 of the present invention may require a neurosurgeon to create a more invasive incision in the patient's scalp. For example, referring again to FIGS. 11*a* and 11*b*, it may be desirable to use a low profile device that is not substantially cylindrical, but instead is substantially planar or concave so as to conform to the curvature of the patient's skull. Such embodiments may require general anesthesia and/or a surgeon to implant the device.

The physician may implant any desired number of sensors in the patient. In some embodiments, between about 1 and about 32 channels (e.g., electrodes) are provided, and preferably between about 8 and about 16 channels are provided. As noted above, in addition to monitoring brain signals, one or more additional implanted sensors may be implanted to measure other physiological signals (e.g., temperature, oxygenation, pulse rate) from the patient.

While it may be possible to implant the implantable sensors under the skull and in or on the brain, it is preferred to implant the implantable sensors in a minimally invasive fashion under at least one layer of the patient's scalp and above the skull. Implantable sensors may be implanted between any of the layers of the scalp (i.e., sub-galeal). For example, the internal devices may be positioned between the skin and the connective tissue, between the connective tissue and the epicranial aponeurosis/galea aponeurotica, between the epicranial aponeurosis/galea aponeurotica and the loose areolar tissue, between the loose areolar tissue and the pericranium, and/or between the pericranium and the calvarium. In some configurations, it may be useful to implant different implantable sensors between different layers of the scalp.

On the other hand, in some embodiments, it may be desirable utilize a less invasive system. In such embodiments, the internal device 102 (or portions thereof) is not actually implanted, but is instead worn or attached to the outer surface of the skin with adhesive or a bandage so as to maintain contact with the patient's skin. For example, it may be possible to surface mount one or more of the sensors behind the ears, in the scalp, on the forehead, along the jaw, or the like. Because the electrodes are wireless and have a small size, the visual appearance of the electrodes may be minimal.

In certain embodiments, the external device 104 provides an indication of the patient's neurological state to the patient. For example, the external device 104 may provide an output to the patient in the form of yellow lights, green lights, and red lights. The patient's condition could, alternatively, be indicated by the absence of an output. For example, the system could include a yellow light and a red light, and the lack of either the red light or yellow light being illuminated would indicate the patient is in a safe state. The outputs may be different displays on a screen that is viewed by the patient, different tactile outputs (e.g., vibrations), different sounds, different lights, or any combination thereof. Additionally, such outputs are not limited to the patient, rather the outputs may be provided to a caregiver. Caregivers may include a physician, a nurse, a relative, or the like.

Figure 15:
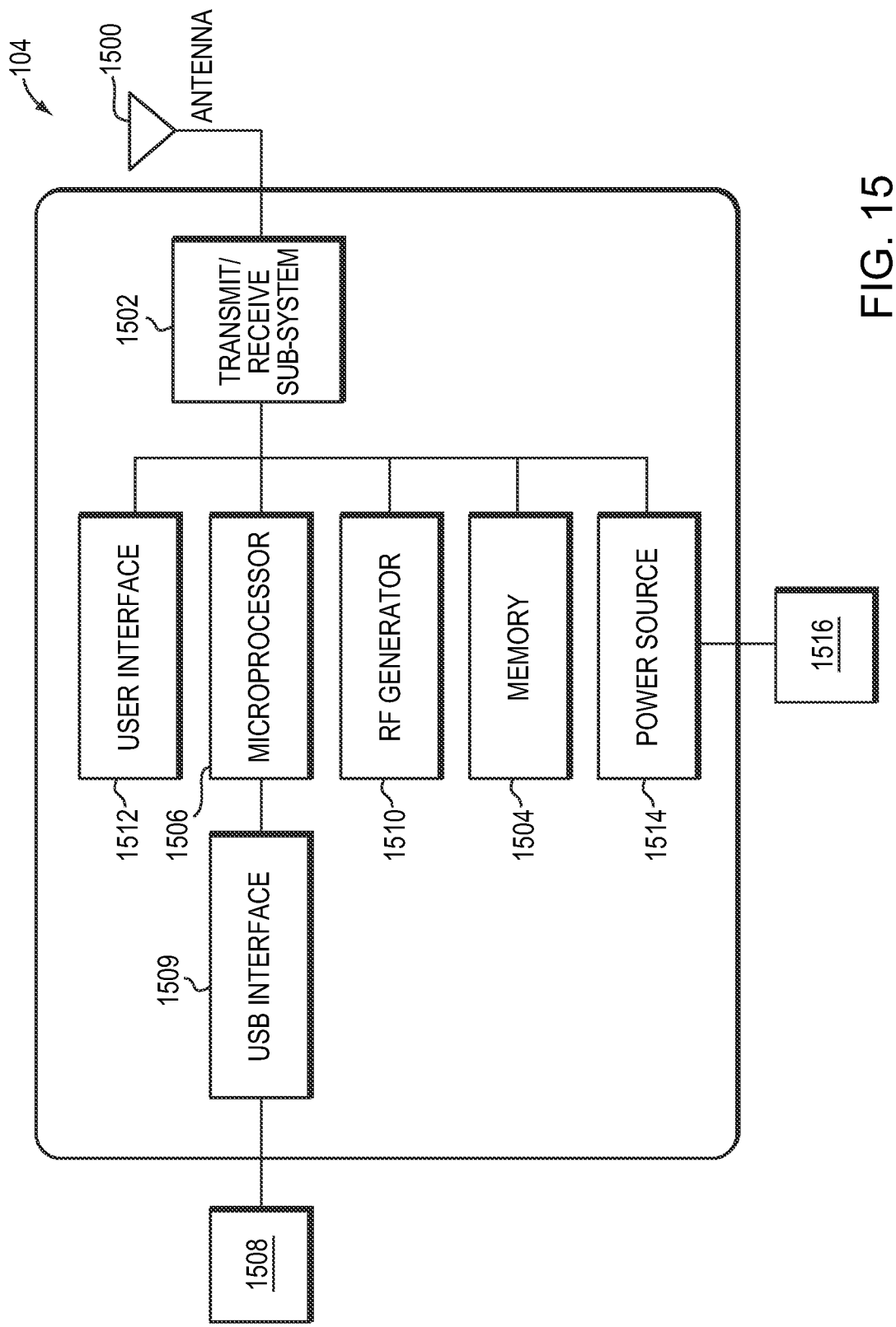
FIG. 15 is a schematic diagram of an external device for processing neurological signals, in accordance with one embodiment of the invention.

FIG. 15 is a schematic illustration of some of the components that may be included in the external device 104, in accordance with certain embodiments of the invention. An antenna 1500 and a transmit/receive subsystem 1502 may receive a data signal (e.g., EEG data) from the internal device 102. The EEG data may include a raw EEG signal, a processed EEG signal, extracted features from the EEG signal, an answer from an implanted EEG analysis software (e.g., safety, prediction, and/or detection algorithm), or any combination thereof. The EEG data may be stored in a memory 1504, such as a hard drive, RAM, permanent or removable Flash Memory, or the like, and/or be processed by a microprocessor 1506 or other dedicated circuitry. In certain embodiments, the microprocessor 1506 includes, is the same as, or is a component of the processing unit 112, described above. At the microprocessor 1506, the data may optionally undergo additional processing. For example, if the EEG data is encrypted, it may be decrypted. The microprocessor 1506 may also include one or more filters that filter out high-frequency artifacts (e.g., muscle movement artifacts, eye-blink artifacts, chewing artifacts, etc.) or subtract an artifact signal (e.g., received by the double-sided electrode), so as to prevent contamination of the sampled EEG signals. In some embodiments, the microprocessor 1506 processes the EEG data to measure the patient's brain state, detect seizures, predict the onset of a future seizure, generate metrics/measurements of seizure activity, or the like.

It should be appreciated, however, that in some embodiments some or all of the computing power of the system of the present invention may be performed in a computer system or a workstation 1508 that is separate from the internal and external devices 102, 104, and that the external device 104 may simply be used as a data collection device. In such embodiments, the workstation 1508 may be located at a physician's office or at the patient's home and the EEG data stored in the memory 1504 may be uploaded to the workstation via a USB interface 1509, removal of the memory (e.g., a Flash Memory stick), or other conventional communication protocols (e.g., a modem).

In one embodiment, the external device 104 includes an RF signal generator 1510 configured to generate an RF field for interrogating and optionally powering the internal device 102. The external device 104 may also include a user interface 1512 for displaying outputs to the patient and for receiving inputs from the patient. The user interface 1512 may include outputs such as auditory devices (e.g., speakers), visual devices (e.g., LCD display, LEDs to indicate brain state or propensity to seizure), tactile devices (e.g., vibratory mechanisms), or the like, and inputs, such as a plurality of buttons, a touch screen, and/or a scroll wheel.

The user interface 1512 may be adapted to allow the patient to indicate and record certain events. For example, the patient may indicate that medication has been taken, the dosage, the type of medication, meal intake, sleep, drowsiness, occurrence of an aura, occurrence of a neurological event, or the like. Such inputs may be used in conjunction with the recorded EEG data to improve the analysis of the patient's condition and determine the efficacy of the medications taken by the patient.

An LCD display of the user interface 1512 may be used to output a variety of different communications to the patient including status of the device (e.g., memory capacity remaining), battery state of one or more components of system, whether or not the external device 104 is within communication range of the internal device 102, brain state indicators (e.g., a seizure warning, a seizure prediction, unknown brain state, a safety indication, a recommendation, or the like). In certain embodiments, the external device 104 includes different colored LEDs to indicate different brain states. For example, a green LED may indicate a safe brain state, a yellow light may indicate an unknown brain state, and a red light may indicate either a seizure detection or seizure prediction.

In certain embodiments, the external device 104 includes a power source 1514 that is in communication with at least one other component of external device 104. The power source may be rechargeable. If the power source is rechargeable, the power source may optionally have an interface for communication with a charger 1516. In one embodiment, external device 104 includes a clock circuit (e.g., oscillator and frequency synthesizer) to provide a time base for synchronizing the external device 104 and the internal device 102.

Some embodiments of the monitoring system may include an integral patient diary functionality. The patient diary may be a module in the external device 104 that allows the patient to input background information for the sampled EEG signals. For example, if a seizure is recorded, the seizure diary may provide insight regarding a trigger to the seizure, or the like. The diary may automatically record the time and date of the entry by the patient. Entries by the patient may be input through a voice recording and/or through activation of user inputs on the user interface 1512. The diary may be used to indicate the occurrence of an aura, occurrence of a seizure, the consumption of a meal, missed meal, delayed meal, activities being performed, consumption of alcohol, the patient's sleep state (drowsy, going to sleep, waking up, etc.), mental state (e.g., depressed, excited, stressed), intake of their medications, medication changes, missed dosage of medication, menstrual cycle, illness, or the like. Thereafter, the patient inputs recorded in the diary may also be used by the physician in assessing the patient's epilepsy state and/or determining the efficacy of the current treatment. Furthermore, the physician may be able to compare the number of seizures logged by the patient to the number of seizures detected by the seizure detection algorithm.

In certain embodiments, with reference back to FIGS. 1 and 2, the inductive coil members 116 include or consist essentially of stainless steel, a high strength alloy such as MP35N, or a combination of materials, such as an MP35N outer layer with a silver core. The inductive coils 116 may be used as antennas to facilitate the wireless transmission of power and data between the internal device 102 and the external device 104 (or other device). In preferred embodiments, the inductive coils 116 may be used to receive and transmit radiofrequency signals. In alternative embodiments, however, the inductive coils 116 may be inductively coupled to external coils to receive energy from a modulating, alternating magnetic field. Furthermore, it may be desirable to use a substantially flat antenna (similar to RFID tags) to facilitate the transmission of power and data.

In certain embodiments, the external device 104 is configured to receive and record data or signals from the internal device 102. The data collection device is typically of a size so as to be portable and carried by the patient, for example as an earpiece or in a pocket or bag that is maintained in close proximity to the patient. In alternative embodiments, the external device 104 may be configured to be used in a hospital setting and placed alongside a patient's bed. As mentioned, communication between the external device 104 and the internal device 102 typically takes place through wireless communication. The external device 104 may include a control module that communicates with the internal device 102 through an antenna.

In various embodiments, to facilitate the transmission of power and data, the antennae of the external device 104 and the internal device 102 are in communication range of each other. The frequency used for the wireless communication link has a direct bearing on the communication range. Typically, the communication range is less than a few inches, less than about one foot, or between about one foot and about twenty feet. As can be appreciated, however, the present invention is not limited to such communication ranges, and larger or smaller communication ranges may be used. For example, if an inductive communication link is used, the communication range may be less than a few inches. In one embodiment, the external device 104 communicates with another device (e.g., a cellular phone, a computer, or a workstation) using a long-range wireless approach, such as BLUETOOTH®.

In some situations, the external device 104 includes an interface that directly links up to the internal device 102 positioned below the patient's skin. For example, the interface may take the form of an electrically or magnetically attached transducer, as with cochlear implants. In various embodiments, the interface enables power to be continuously delivered to the internal device 102 and provides higher rates of data transmission.

In some configurations, the systems described herein include one or more intermediate transponders that facilitate data transmission and/or power transmission between the internal device 102 and the external device 104. The intermediate transponder may be implanted in the patient or it may be external to the patient. If implanted, the intermediate transponder will typically be implanted between the internal device 102 and the expected position of the external device 104 (e.g., in the neck, chest, or head). If external, the transponder may be attached to the patient's skin, positioned on the patient's clothing or other body-worn assembly (e.g., eyeglasses, cellular phone, belt, hat, earpiece, etc.), or in a device that is positioned adjacent the patient (e.g., a pillow, chair headrest, etc.). The intermediate transponder may be configured to transmit power, transmit data, or both data and power. By including an intermediate transponder, the external device 104 may be placed outside of its normal communication range from the implanted device 102 (e.g., on a patient's belt or in a patient's bag), and still be able to receive data from the internal device 102 and/or transmit power to the internal device 102.

In certain embodiments, transmission of data and power between the internal device 102 and the external device 104 is carried out through a radiofrequency link, magnetic induction, an electromagnetic link, a BLUETOOTH® link, a Zigbee link, a sonic link, an optical link, other types of wireless links, and/or combinations thereof. In certain embodiments, data is wirelessly transmitted using a radiofrequency link, similar to the link used with radiofrequency identification (RFID) tags.

In certain embodiments, the internal device 102 and the external device 104 of the present invention use an electromagnetic field/high frequency communication link to both illuminate the internal device 102 and enable high data transfer rates. By comparison, previous systems have used an internally powered internal device 102 and use a slower communication link (e.g., that is designed for long link access delays) to transmit data out on a non-continuous basis. In contrast, some embodiments of the present invention use a fast access communication link that transmits smaller bursts of data (e.g., a single or small number of EEG samples at a time) on a substantially continuous basis.

In various embodiments, the frequencies used to illuminate and transfer data between the internal device 102 and the external device 104 are between 1 MHz and 1 GHz, between 1 MHz and 50 MHz, and/or between 400 MHz and 2.4 GHz (e.g., when using radio-frequency transmission). As can be appreciated, while the aforementioned frequencies are the preferred frequencies, the present invention is not limited to such frequencies and other frequencies that are higher and lower may also be used. For example, it may be desirable us use the MICS (Medical Implant Communication Service band) that is between 402-405 MHz to facilitate the communication link. In Europe, it may be desirable to use the ETSI RFID allocation of 869.4-869.65 MHz.

In certain embodiments, the system of the present invention makes use of forward error correction ("FEC") methods to control errors and ensure the integrity of the data transmitted from the internal device 102 to the external device 104. The forward error correction methods may include such conventional implementations as a cyclic redundancy check ("CRC"), checksums, or the like.

If desired, the data signals that are wirelessly transmitted from the internal device 102 may be encrypted prior to transmission to the external device 104. Alternatively, the data signals may be transmitted to the external device 104 as unencrypted data and, at some point prior to the storage of the data signals or prior to transfer of the data signals to the physician's office, the EEG data may be encrypted so as to help ensure the privacy of the patient data.

In certain embodiments, the internal device 102 is passive or semi-passive and is a "slave" to the "master" external device 104. For example, the internal device 102 may remain dormant until it is interrogated and possibly energized by an appropriate RF signal from the external device 104. In one embodiment, the internal device 102 has minimal electronic components and computing power to provide a small package size for implantation.

In certain embodiments, the EEG analysis systems are embodied in the internal device 102, the external device 104, or both the internal device 102 and the external device 104. For example, in one embodiment, the algorithms for determining the patient's neurological state are fully stored in and processed by the internal device 102. In such embodiments, the patient's propensity for a neurological event is calculated in the internal device 102 and a data signal is transmitted to the external device 104. The external device 104 performs any remaining processing to generate and provide the communication output to the patient. Such embodiments have the benefit of maintaining processing within the patient, while reducing the communications demands on the system.

In other embodiments, the signals sampled from the patient may be partially processed in the internal device 102 before transmitting data to the external device 104 so as to reduce the total amount of data to be transmitted, thereby reducing the power demands of the transmit/receive subsystem. Examples include: digitally compressing the signals before transmitting them; encrypting the signals; selecting only a subset of the measured signals for transmission; selecting a limited segment of time and transmitting signals only from that time segment; extracting salient characteristics of the signals; transmitting data representative of those characteristics rather than the signals themselves; and transmitting only the result of classification. Further processing and analysis of the transmitted data may then take place in the external device 104.

In yet other embodiments, it may be possible to perform some of the signal processing in the internal device 102 and some of the signal processing in the external device 104. For example, one or more characteristics from the one or more signals may be extracted with feature extractors in the internal device 102. Some or all of the extracted characteristics may be transmitted to the external device 104 where the characteristics may be classified to assess the patient's susceptibility for a neurological event. If desired, external device 104 may be tailored to the individual patient. Consequently, the classifier may be adapted to allow for transmission or receipt of only the characteristics from the internal device 102 that are useful for that individual patient.

In one embodiment, predictions of seizure activity are enhanced through a training process in which the system learns to recognize patient-specific indicators of seizure activity. For example, the system may be used to monitor the patient's neurological signals and the patient's artifact signals over a span of days or weeks. By correlating the neurological signals with true neurological events (e.g., seizures), the system's ability to predict seizure activity may improve. Likewise, in certain embodiments, the system learns the patterns and sources of artifacts and uses known patterns to better distinguish between artifacts and true neurological signals. For example, the system may utilize other sensors (e.g., force transducers or accelerometers) to correlate artifacts with patient movement. By recognizing the patient's specific causes of artifacts and the characteristic signatures of artifacts in the detected signals, the system is better able to mitigate the effects of the artifacts. The result of the training process is an enhanced ability to predict neurological events.

In certain embodiments, the system includes one or more algorithms or modules that process input data (e.g., data from the sensors). The algorithms may take a variety of different forms, and may include the use of feature extractors (e.g., for identifying features in the neurological signals) and classifiers (e.g., for determining a seizure state based on the features). The input data (e.g., EEG data) used by the algorithms may be in the form of analog signal data or digital signal data that has been converted by way of an analog to digital converter. The signals may also be amplified, preprocessed, and/or conditioned to filter out spurious signals or noise. In one embodiment, the input data includes between about 1 channel and about 64 channels of EEG from the patient.

In various embodiments, the input data is supplied to the one or more feature extractors, which may utilize, for example, a set of computer executable instructions stored on a computer readable medium, or a corresponding instantiated object or process that executes on a computing device. Certain feature extractors may also be implemented as programmable logic or in a fixed logic device. In general, feature extractors process data and identify some characteristic of interest in the data.

Each feature extractor may be univariate (operating on a single input data channel), bivariate (operating on two data channels), or multivariate (operating on multiple data channels). Some examples of potentially useful characteristics to extract from signals for use in determining the patient's propensity for a neurological event include but are not limited to bandwidth limited power (alpha band [8-13 Hz], beta band [13-18 Hz], delta band [0.1-4 Hz], theta band [4-8 Hz], low beta band [12-15 Hz], mid-beta band [15-18 Hz], high beta band [18-30 Hz], gamma band [30-48 Hz], high frequency power [>48 Hz], bands with octave or half-octave spacings, wavelets, etc.), second, third and fourth (and higher) statistical moments of the EEG amplitudes or other features, spectral edge frequency, decorrelation time, Hjorth mobility (HM), Hjorth complexity (HC), the largest Lyapunov exponent L(max), effective correlation dimension, local flow, entropy, loss of recurrence LR as a measure of non-stationarity, mean phase coherence, conditional probability, brain dynamics (synchronization or desynchronization of neural activity, STLmax, T-index, angular frequency, and entropy), line length calculations, first, second and higher derivatives of amplitude or other features, integrals, and mathematical linear and non-linear operations including but not limited to addition, subtraction, division, multiplication and logarithmic operations. Of course, for other neurological conditions, additional or alternative characteristic extractors may be used with the systems described herein.

In various embodiments, the extracted characteristics are supplied to the one or more classifiers. Like the feature extractors, each classifier may be, for example, a set of computer executable instructions stored on a computer readable medium or a corresponding instantiated object or process that executes on a computing device. Certain classifiers may also be implemented as programmable logic or in a fixed logic device.

The classifiers analyze one or more of the extracted characteristics, and either alone or in combination with each other (and possibly other patient dependent parameters) provide a result that may characterize, for example, a patient's condition. The output from the classifiers may then be used to determine the output communication that is provided to the patient regarding the patient's condition. As described above, the classifiers may be trained by exposing them to training measurements. Some examples of classifiers include k-nearest neighbor ("KNN"), binary and higher order space partitions, linear or non-linear regression, Bayesian, mixture models based on Gaussians or other basis functions, neural networks, and support vector machines ("SVM"). Each classifier may provide a variety of output results, such as a logical result or a weighted result. The classifiers may be customized for the individual patient and may be adapted to use only a subset of the characteristics that are most useful for the specific patient. Additionally, over time, the classifiers may be further adapted to the patient, based, for example, in part on the result of previous analyses and may reselect extracted characteristics that are used for the specific patient.

In certain embodiments, the classifiers have multiple classes (e.g., two or more), provide a weighted answer, and/or provide an output that is expressed as a continuum between the safe and pro-seizure conditions. A scalar or vector of parameters may describe the actual condition and its variations. For example, a multiple class classifier may utilize or provide labels such as "between-seizures," "pro-seizure," "seizure," and/or "post-seizure." In other embodiments, the classifiers are one-class classifiers that calculate probability of class membership (e.g., probability of pro-seizure, probability of safe).

Any number and type of classifier may be used by the systems of the present invention. For example, in certain embodiments it may be desirable to have a single classifier classify the patient as being in one of three conditions—a between-seizures class, a pro-seizure class, and a safe class—which could correspond, respectively, to a normal propensity for a future seizure, an elevated or high propensity for a future seizure, and a low propensity for a future seizure.

In certain embodiments, the systems and methods described herein employ a stimulation method for predicting the patient's neurological condition and onset of neurological events (e.g., seizures). The stimulation method includes determining a characteristic neurological response to an applied stimulation for a patient's different neurological states. For example, in one embodiment, the patient's brain is stimulated (e.g., with electrical energy, RF energy, optical energy, and/or acoustic energy) and the characteristic neurological response is measured and determined for each of the patient's neurological states (e.g., a between-seizures state, an inter-ictal discharge, a pro-seizure state, and a safe state). In one embodiment, the source of the stimulation is one or more of the sensors. Once the characteristic neurological responses have been determined, the patient may be regularly stimulated, and the neurological responses measured, to determine the patient's neurological state at a given time. Advantageously, this approach of actively stimulating the patient's brain and measuring the neurological response allows the patient's neurological state to be more accurately determined or predicted than through passive electroencephalography measurements alone (i.e., without stimulation). In certain embodiments, this stimulation method enables more accurate determinations of the patient's neurological state and predictions of neurological events.

In certain embodiments, the system utilizes a closed loop or open loop therapeutic response that attempts to minimize and/or prevent a seizure occurrence. Such therapeutic approaches may include, without limitation, vagus nerve stimulation, deep brain stimulation, neurostimulation, automated/semi-automated or manual dispensing of antiepileptic drugs, and biofeedback techniques.

In various embodiments, the systems described herein generate an output based on a determination of the patient's brain state. The output may be in the form of a control signal to activate a therapeutic device (e.g., implanted in the patient, such as a vagus nerve stimulator, deep brain or cortical stimulator, implanted drug pump, etc.). In other embodiments, the output may be used to activate a user interface on the external device 104 to produce an output communication to the patient. For example, the external device 104 may be used to provide a substantially continuous output or periodic output communication to the patient that indicates the patient's state and/or propensity for the neurological event. Such a communication could allow the patient to manually initiate therapy (e.g., wave a wand over an implanted vagus nerve, cortical, or deep brain stimulator, take a fast acting AED, etc.) or find a safe place.

Furthermore, in some embodiments, it may be desirable to modify the sensor or other portions of the internal device 102 to provide stimulation to the patient. For example, the internal device 102 may include a pulse generator and associated hardware and software for delivering stimulation to the patient through the electrodes of the sensors. In other embodiments, the internal device 102 includes one or more transducers for delivering electrical stimulation (A.C. and/or D.C.), RF stimulation, acoustic stimulation, ultrasonic stimulation, magnetic stimulation, and/or light stimulation (e.g., using LEDs). In one embodiment, the internal device 102 includes a drug delivery device. In certain embodiments, the external device 104 may include the hardware and software to generate the control signals or instructions for delivering the stimulation to the patient.

The EEG systems and devices described herein can be employed as chronic epilepsy monitoring devices, particularly for drug-resistant epileptics. Realistically, 50,000 patients in the United States may benefit from use of the device, and a much greater number would benefit worldwide, as 95% of epilepsy cases are in developing countries. In particular, there are approximately 150,000 new cases of epilepsy in the United States every year, and 50 million people worldwide have epilepsy. The systems and methods may also be employed as sleep disorder monitoring and prevention devices. Sleep disorders, such as insomnia, apnea, and narcolepsy, can greatly deteriorate mental health and quality of life. Post-traumatic stress disorder and/or traumatic brain injury may contribute to the development of these sleep disorders.

In certain embodiments, the systems and methods described herein are used to identify a safe condition for each patient in which the patient is highly unlikely to transition to a seizure state within a specified time period. While it is beneficial to the patient to know if the patient is in the between-seizures condition, being in the between-seizures condition does not necessarily inform the patient that they will not quickly transition from the between-seizures condition to the seizure condition. Being able to inform a patient that they are in a safe state can allow the patient to engage in normal daily activities, such as walking down a set of stairs, without fearing that they will have a seizure or without fearing that they may quickly transition into a pro-seizure state (i.e., a state that represents a high susceptibility for seizure). Knowing when a seizure is unlikely to occur can be even more important to the patient's freedom than being alerted to when a seizure is likely to occur.

While the discussion herein focuses generally on measuring electrical signals generated by electrodes placed near the brain of patients for the prediction of seizure activity, it should be appreciated that the invention is not limited to measuring EEG signals or to seizure prediction. For example, the systems and methods described herein could also be used to measure one or more of blood pressure, blood oxygenation (e.g., via pulse oximetry), temperature of the brain or of portions of the patient, blood flow, ECG/EKG, heart rate signals, respiratory signals, chemical concentrations of neurotransmitters, chemical concentrations of medications, pH in the blood, or other physiological or biochemical parameters of a patient.

Furthermore, the systems and methods described herein may also be applicable to monitoring other neurological or psychiatric disorders and identifying or predicting a condition or state for such disorders. For example, the present invention may also be applicable to monitoring and management of sleep apnea, Parkinson's disease, essential tremor, Alzheimer's disease, migraine headaches, depression, eating disorders, cardiac arrhythmias, bipolar spectrum disorders, or the like. As can be appreciated, the features extracted from the signals and used by the algorithms will be specific to the underlying disorder that is being managed. While certain features may be relevant to epilepsy, such features may or may not be relevant to the state measurement for other disorders.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. An electro-encephalography system, comprising:
   (a) an internal device for implantation below a scalp and above a skull of a patient, the internal device comprising:
      (i) a first electrode disposed on a first side of the internal device for receiving a first signal comprising neurological signals originating from the patient's brain and artifacts originating from sources other than the patient's brain, the first signal comprising a first ratio of the neurological signals to the artifacts;
      (ii) a second electrode disposed on a second side of the internal device for receiving a second signal comprising the artifacts; and
      (iii) a therapy device for providing therapy to the patient; and
   (b) an external device in wireless communication with the internal device, the external device to be worn or carried outside the patient's body, the external device comprising a processing unit for:
      (i) providing power to the internal device;
      (ii) receiving data from the first and second electrodes, the data comprising the first and second signals;
      (iii) processing the received data by subtracting at least a portion of the second signal received from the second electrode disposed on the second side of the internal device from the first signal received from the first electrode disposed on the first side of the internal device;
      (iv) determining a neurological state of the patient based on the processed signal; and
      (v) transmitting instructions to the therapy device for providing therapy to the patient according to the neurological state.

2. The system of claim 1, wherein the processing unit records at least one of the processed signal or the data received from the first and second electrodes.

3. The system of claim 1, wherein the first side of the internal device is opposite the second side of the internal device.

4. The system of claim 1, wherein the therapy device comprises at least one of the first electrode or the second electrode.

5. The system of claim 1, wherein the therapy provided to the patient is selected from the group consisting of electrical stimulation, acoustic stimulation, RF stimulation, ultrasound stimulation, magnetic stimulation, electro-magnetic stimulation, photon stimulation, and a pharmaceutical compound.

6. The system of claim 1, wherein the second electrode is configured for implantation in a muscle artifact location.

7. The system of claim 1, wherein the processing unit determines the neurological state of the patient based on data received from the first and second electrodes in response to stimulation of the patient's brain.

8. The system of claim 1, wherein the neurological state is indicative of a propensity for a seizure.

9. The system of claim 1, wherein the processing unit provides trans-cutaneous wireless power to the internal device.

10. The system of claim 1, wherein the artifacts originate from a source selected from the group consisting of the patient's scalp, the patient's eyes, electromyographic signals, and motion.

11. The system of claim 1, wherein the external device comprises an earpiece.

12. The system of claim 1, wherein the external device comprises at least one sensor for sensing at least one of the patient's temperature, cardiac pulse-rate, or tissue oxygenation level.

13. The system of claim 1, wherein the external device comprises at least one inertial sensor for sensing at least one of a heading, a motion, or an orientation of the processing unit.

14. The system of claim 1, wherein the external device comprises a temperature sensor for measuring the patient's temperature.

15. The system of claim 1, wherein the external device comprises an audible alarm for warning the patient of an onset of a seizure.

16. The system of claim 1, wherein the external device comprises at least one of a modem or a transceiver.

* * * * *